United States Patent

Bruno

[11] Patent Number: 4,511,577
[45] Date of Patent: Apr. 16, 1985

[54] DERIVATIVES OF BENZOIC ACID

[75] Inventor: Graziella Bruno, Milan, Italy

[73] Assignee: Media Research s.r.l., Milan, Italy

[21] Appl. No.: 589,126

[22] Filed: Mar. 13, 1984

[30] Foreign Application Priority Data

Mar. 23, 1983 [IT] Italy .............................. 20235 A/83

[51] Int. Cl.³ ..................... A61K 31/38; C07D 333/24
[52] U.S. Cl. ....................................... 514/448; 549/71
[58] Field of Search ........................... 549/71; 424/275

[56] References Cited

PUBLICATIONS

Vega, Chem. Abstr., 94:30556u, (1981).
Remington's Pharm. Sciences, 15th ed., (1975), pp. 1048, 1049.

Primary Examiner—Alan Siegel
Attorney, Agent, or Firm—Bucknam and Archer

[57] ABSTRACT

A novel derivative of benzoic acid, 2-(2-thenoyloxy)-benzoic acid of formula (I)

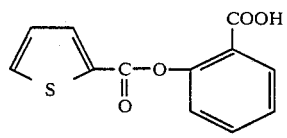

and pharmaceutically acceptable salts thereof with alkali and alkali-earth metals and with basic amino acids such as lysine, arginine and histidine are valuable antiinflammatory and analgesic agents.

They may be prepared by reacting acetylsalicylic acid with a reactive derivative of 2-thiophenecarboxylic acid.

The compounds of the invention may be formulated with conventional pharmaceutically acceptable carriers or diluents, to provide a pharmaceutical composition.

4 Claims, No Drawings

DERIVATIVES OF BENZOIC ACID

The present invention relates to 2-(2-thenoyloxy)-benzoic acid of formula (I)

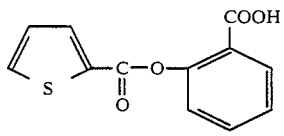

The present invention relates also to pharmaceutically acceptable salts of compound (I) with alkali and alkali-earth metals and with basic amino acids; the 2-(2-thenoyloxy)-benzoic acid lysine salt being particularly preferred.

Compound (I), which will be hereinafter called MR-Y134 for sake of shortness, and its pharmaceutically acceptable salts are advantageously employed in therapy.

MR-Y134 may be prepared by reacting acetylsalicylic acid with a reactive derivative of 2-thiophenecarboxylic acid, such as an anhydride or an acyl halide.

When an acyl halide is employed, it is necessary to carry out the reaction in the presence of an acid-binding agent, which may be an organic base (e.g. pyridine or triethylamine) or an inorganic base (e.g. an alkali metal carbonate or hydrogenocarbonate).

The reaction is preferably carried out in the presence of a solvent, the nature of which is not critical, provided that it has no adverse effect upon the reaction.

The reaction is preferably carried out in pyridine/halogenated aliphatic hydrocarbons mixtures.

The addition of acetylsalicylic acid is suitably effected at temperatures ranging from 0° to +10° C., with cooling, the reaction being exothermic.

After completion of the reaction, the desired product may be recovered from the reaction mixture by conventional means. For example, the reaction mixture may be concentrated by evaporation under reduced pressure, after which the obtained residue is extracted with an organic solvent, then the solvent is distilled off from the extract to give the desired compound, which may, if necessary, be further purified by such conventional techniques as recrystallization or column chromatography.

The preparation of MR-Y134 is further illustrated by the following non-limiting example.

EXAMPLE

To 7.5 g of 2-thiophencarboxylic acid chloride (5.5 cc) dissolved in 20 cc of methylene chloride, was added a solution of 7 g of salicylic acid in 100 cc of methylene chloride and 12 cc of pyridine, under stirring, keeping the temperature at 0°–5° C. The reaction was exothermic. Then the temperature was raised to 40° C., and the reaction mixture was maintained at this temperature for 3 hours. After evaporation under vacuum to dryness, the residue was treated with $H_2O$/sodium hydrogenocarbonate, washed with diethyl ether, extracted with diluted hydrochloric acid and stirred for 30 minutes in ice-water.

Finally the filtrate was thoroughly washed with water. Yield: 8.5 g. M.p.=102°–105° C.

I.R. Spectrum (nujol mull; the values of absorption bands are given in $cm^{-1}$): stretch C=O acid and ester/1720–1700 (broad band) $H^1$ N.M.R. Spectrum (registered in DMSO, internal standard TMS, the values of chemical shifts are given in δ): 5.2 (s, 1H, mobile OH); 7.2–8.1 (m, 7H, aromatics).

ANTIINFLAMMATORY ACTIVITY

The antiinflammatory activity of MR-Y134 in comparison with acetylsalicylic acid was determined by the test of carrageenin induced oedema in rat paw, according to the method of Winter, Rissly, Ness. (Proc. Soc. Exp. Biol. Med., 111, 544–547, 1962).

The oedema was induced in the animals by injecting in their paws 0.1 ml of a 1.5% carrageenin solution, and the activity of MR-Y134 was determined in comparison with equal doses by weight of acetylsalicylic acid (ASA). The paw volume was determined using an apparatus supplied by U. Basile Ltd.

The results reported in Table I clearly show that MR-Y134 has a good antiinflammatory activity, substantially equal to the one of ASA, even if they are administered in equal amounts by weight.

TABLE I

Antiinflammatory activity.
*Carrageenin oedema* in rat paw.
Volume of rat paw in $mm^3$ (control: 1% gum arabic-ASA and MR-Y134: 75 mg/kg per os).

| TREATMENT | N° ANIMALS | PAW AVERAGE VOLUME ($mm^3$) | | | | | |
|---|---|---|---|---|---|---|---|
| | | Basal | 30' | 1h | 2h | 3h | 6h |
| CONTROL | 5 | 1.53 | 1.84 | 1.92 | 2.02 | 2.29 | 3.16 |
| ASA | 5 | 1.55 | 1.69 | 1.75 | 1.79 | 1.81 | 2.49 |
| MR-Y134 | 5 | 1.58 | 1.71 | 1.82 | 1.80 | 1.90 | 2.79 |

Percent variation with respect to 0 time

| TREATMENT | TIME | | | | | AREA Δ % | % inhibition versus control |
|---|---|---|---|---|---|---|---|
| | 30' | 1h | 2h | 3h | 6h | | |
| CONTROL | 22.14 | 27.29 | 35.67 | 53.51 | 92.10 | 243.3 | — |
| ASA | 9.71 | 13.57 | 16.30 | 17.71 | 62.13 | 113.35 | 53.41 |
| MR-Y134 | 8.03 | 14.96 | 14.18 | 20.46 | 76.48 | 127.69 | 47.51 |

ANALGESIC ACTIVITY

The analgesic activity was determined according to the tail-flick test, employing an apparatus supplied by Socrel Ltd., Milano, Italy.

The data reported in Table II show that MR-Y134 exhibits a remarkable analgesic activity which, under the experimental conditions, is three times higher than the one of ASA, although the latter has been administered in equal amounts by weight.

TABLE II

Tail-flick (for analgesia)
Reaction times in seconds

| TREATMENT | DOSE mg/kg os | TIMES | | | |
|---|---|---|---|---|---|
| | | Basal | 1h | 3h | 6h |
| CONTROL | — | 9.34 | 6.30 | 6.46 | 6.56 |
| ASA | 75 | 9.30 | 7.16 | 6.82 | 6.76 |
| MR-Y134 | 75 | 9.82 | 8.9 | 7.96 | 8.28 |

Percent variation with respect to 0 time

| TREATMENT | TIMES | | | AREA Δ % | % inhibition versus control |
|---|---|---|---|---|---|
| | 1h | 3h | 6h | | |
| CONTROL | 32.54 | 30.8 | 29.76 | 170.45 | — |
| ASA | 23.01 | 26.66 | 27.31 | 142.13 | 16.61 |

TABLE II-continued

Tail-flick (for analgesia)
Reaction times in seconds

| MR-Y134 | 9.36 | 18.94 | 15.68 | 84.91 | 50.18 |
|---|---|---|---|---|---|

Gastro-injuring action

The action on the gastric mucosa of MR-Y134 in comparison with equimolecular doses of ASA was determined according to the method described by Pisanti and Volterra (Il Farmaco, vol. 25, (2), 105).

The products were administered orally.

Male Sprague-Dawley rats were used fastened for 48 hours with water ad libitum.

The control group was administered with the solvent only (1% carboxymethylcellulose).

The obtained results clearly show that MR-Y134 administered orally, present a scarce gastro-injuring activity, substantially lower than the one of ASA, on the ground of the method and doses employed.

PHARMACOKYNETICS

The plasmatic kynetic of acetylsalicylic acid in rat was compared after oral administration of equimolecular doses of MR-Y134 and sodium salicylate (466 mg/kg MR-Y134 and 300 mg/kg ASA respectively).

The compounds were both administered in the form of 2% gum arabic suspension to rats fastened for 12 hours. Each animal was administered with 1.0 ml of solution.

The rats were killed at the following times: 1, 2, 4, 8, 12 hours after the administration of the compounds.

The blood sample was drawn in heparin.

The results reported in Table III clearly show that MR-Y134 presents a kynetic profile better than the one of sodium salicylate. In fact, MR-Y134 administered in doses equimolecular with sodium salicylate, allows to reach plasmatic levels virtually comparable until the second hour, after which the sodium salicylate peak appears, while the MR-Y134 peak appears around the third hour and is substantially higher.

The values obtained at the subsequent times show that the MR-Y134 concentrations keep values higher than the ones of ASA, exhibiting an higher and more prolonged persistence in the bloodstream such as to promise, in the clinical medicine applications, a decrease of the daily administrations frequency.

TABLE III

Plasmatic concentrations (μg/ml) after oral administration of equimolecular doses of MR-Y134 and sodium salicylate (300 mg/kg sodium salicylate and 466 mg/kg MR-Y134 respectively)

| TIMES (HOURS) | SODIUM SALICYLATE | MR-Y134 |
|---|---|---|
| 1 | 361.8 | 460.6 |
| 2 | 534.1 | 555.4 |
| 4 | 470.5 | 581.9 |
| 8 | 456.2 | 450.7 |
| 12 | 324.8 | 405.6 |

The present invention refers also to all the industrially applicable aspects connected with the use of MR-Y134 as antiinflammatory and analgesic agent.

The invention also provides pharmaceutical compositions containing, as active ingredient, prefixed and therapeutically effective amounts of MR-Y134, in admixture with a pharmaceutically acceptable carrier or diluent to be administered orally, rectally, or parenterally.

Examples of such formulations are tablets, capsules, pills, powders, granules, syrups, suppositories, phials, ampoules, together with suitably excipients commonly used in pharmaceutical technique.

I claim:

1. 2-(2-Thenoyloxy)-benzoic acid of formula (I):

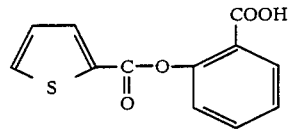

and pharmaceutically acceptable salts thereof.

2. Alkali and alkali-earth metal salts of compound (I), according to claim 1.

3. Pharmaceutical compositions having antiinflammatory and analgesic activity, wherein said compositions comprise, as active ingredient, a compound according to claim 1, and a pharmaceutically acceptable carrier.

4. Pharmaceutical compositions according to claim 3, in form of capsules, tablets, pills, syrups, suppositories, solutions.

* * * * *